United States Patent [19]
Jones et al.

[11] Patent Number: 5,607,479
[45] Date of Patent: Mar. 4, 1997

[54] HAIR LOSS REPLACEMENT METHOD AND SYSTEM

[76] Inventors: Dennis R. Jones; Patricia A. Jones, both of 1001 Fairway Ct., Chesapeake, Va. 23320

[21] Appl. No.: 391,693
[22] Filed: Feb. 21, 1995
[51] Int. Cl.⁶ ..................................... A61F 2/10
[52] U.S. Cl. .............................. 623/15; 132/53
[58] Field of Search ................. 623/15; 600/36; 132/53; 606/187, 133

[56] References Cited

U.S. PATENT DOCUMENTS

| 5,313,963 | 5/1994 | Rennix | 132/54 |
| 5,417,683 | 5/1995 | Shiao | 606/1 |

FOREIGN PATENT DOCUMENTS 2676622  11/1992  France ..................... 623/15

Primary Examiner—David H. Willse
Attorney, Agent, or Firm—Jim Zegeer

[57] ABSTRACT

The process of replacing a person's hair loss involves a combination of medical hair transplants and a non-medical hair piece. A front natural hair line is formed by surgically transplanting hair follicles from one area of the person's head to the frontal area, with micrografts of 1 to 2 hair follicles being located along the most forward portion of the front natural hair line. The front portion or edge of a non-surgical hair piece is customized to fit precisely behind the front natural hair line and to blend into the surgically transplanted hair.

2 Claims, 1 Drawing Sheet

HAIR LOSS REPLACEMENT METHOD AND SYSTEM

The present invention is directed to a process of replacing a man's or woman's hair loss by using a combination of medical hair transplants and a non-medical hair piece.

SUMMARY OF THE INVENTION

According to the invention, hairs are surgically transplanted using any medically accepted technique (but the minigraft/micrograft techniques are preferences) from one area of the person's head to the frontal area of the person's head, to form a front natural line of hair. A non-surgical hair piece has a front portion or edge customized to fit precisely behind the front natural hair line and to blend into the surgically transplanted hair, and then the non-surgical hair piece is attached to the person's scalp. The medical hair transplants can be any one or a combination of mini-grafts, micro-grafts, or incision grafts where hair is removed surgically from one area of the head (usually the sides and back). Slit incisions or sections of the bald scalp are removed and the transplant hair is then placed into the holes or incisions in the bald or balding area.

DESCRIPTION OF THE DRAWINGS

The above and other objects, advantages and features of the invention will become more apparent from the following specification and accompanying drawings wherein.

DETAILED DESCRIPTION OF THE INVENTION

According to the invention, the doctor will usually use micro-grafts which are grafts that consists of 1–2 hairs and mini-grafts which are grafts containing 3–7 hairs. Other hair transplant techniques can be used. The non-surgical hair (see FIG.4) used make up the second component necessary to complete the transplacement process. The foundation 30 for this hair piece can be made from a wide range of materials from polyurethane, mono-filament, silk, or a variety of meshes and can consist of a variety of combinations to meet the activity and lifestyle of the wearer. Then hair 31 (either human hair or a synthetic fiber hair) is tied into the foundation. This hair piece is then attached either to the person's remaining hair or scalp by using two sided tape, glue, sutures, bonding adhesive, or a variation of clips.

Figure 1:
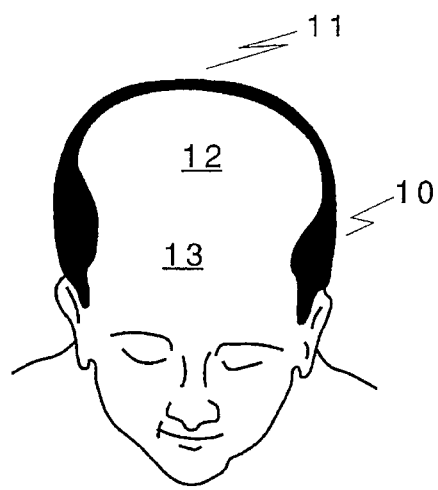
FIG. 1 shows a man with a bald head on top and front.

Referring now to the drawings, FIG. 1 shows a man 10 with a bald head 11 on top 12 and front 13.

Figure 2:
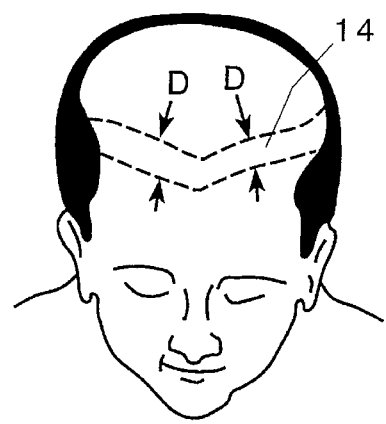
FIG. 2 illustrates the frontal area in which the surgical hair transplants will be performed according to the invention.

FIG. 2 shows a frontal area 14 to which surgical transplants are to be made. Hairs from a patch at the rear (not shown) are transplanted.

Figure 3:
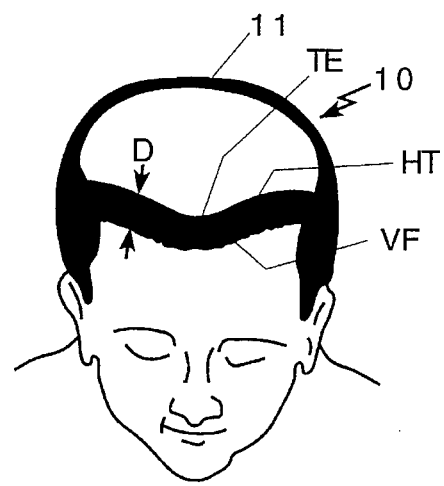
FIG. 3 illustrates surgically transplanted hair forming a frontal area to form a living hair line.

FIG. 3 shows hair transplants HT using mini and micrografts that have been transplanted in the frontal area. Starting with micrografts (1–2 hairs) in the very front VF and extending back to trailing edge TE with micro and mini-grafts (3–5 hairs) a depth D between about 1–2½ inches constituting a line of hair. Hair could be transplanted back a little further to meet a specific person's needs, if desired, but the 1–2½ depth D is acceptable.

Figure 4:
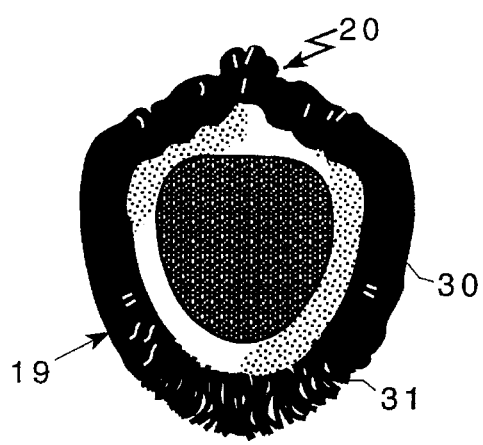
FIG. 4 shows a non-surgical hair piece or replacement in which the front or forward edge is customized to the trailing edge of the frontal area constituting the frontal line of hair.

FIG. 4 shows the non-surgical "Hair Piece", "Hair Replacement" 19, or system (the art has many different names for this non-surgical component). The basic difference in this hair replacement hair piece is the front or leading edge 20. According to the invention, the front 20 is custom-made or customized to fit precisely into or behind the transplanted hair. Usually the front 20 will be sculpted so a not to give a hard look, but to blend into the mini and micro-grafts undetected.

Figure 5:
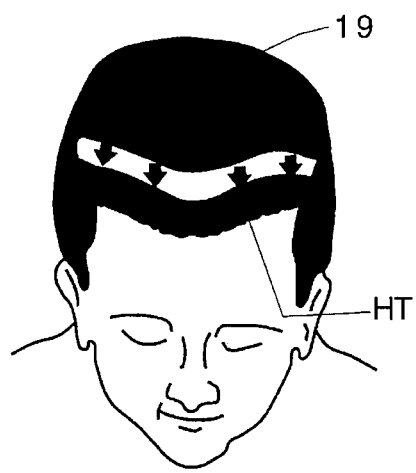
FIG. 5 shows how the hair piece or replacement is fitted to conform or blend with the transplanted line of hair in front.

FIG. 5 shows the hair piece/hair replacement being fitted to conform or blend with the transplanted hair in the front.

Figure 6:
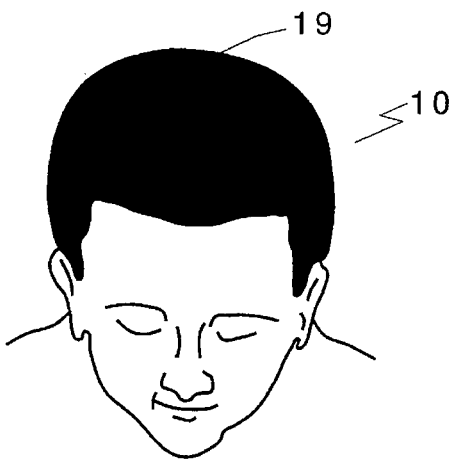
FIG 6 shows the transplanted hair in the front blended with the hair piece or replacement.

FIG. 6 shows the transplanted hair in the front blended with the hair piece/hair replacement. The hair piece/hair replacement is attached either to the client's scalp or existing hair on the sides and back and then styled to blend with their existing hair.

In summary, the process of this invention gives a person who is now wearing a conventional hair piece/hair replacement the ability to still cover the top and back of the head with a hair piece but gives them a totally frontal hair line by using his own hair through transplants using mini and micro-grafts.

This process can be performed on someone who has never worn a hair replacement. It can also take a person who presently wears a hair replacement and perform the process of this invention on them as long as there is enough hair on the sides and the back to support the mini and micro-grafts in the front.

The invention is great for all the men (and women) who wear those awful looking hair pieces. Usually you can match-up the sides and back, but you can usually tell it is a hair piece in he front. This invention will eliminate that problem.

While there has been shown and described preferred embodiments of the invention, it will be appreciated that various other embodiments and modifications and adaptations of the invention will be readily apparent to those skilled in the art and it is intended that such obvious modification, adaptation and variation be encompassed within the claims appended hereto.

What is claimed is:

1. A process for replacing a person's hair loss, comprising the steps of:

surgically transplanting hair follicles from one area of the person's head to the frontal area of the person's head to form a front natural hair line, said step of surgically transplanting hair follicles comprises creating a gradation between minigrafts of 3 to 7 hair follicles and micrografts of 1 to 2 hair follicles, providing a non-surgical hair piece having a front edge portion, customizing said front edge portion by shaping it to fit precisely behind and contiguous to the rear edge of said front natural hair line and to blend into the surgically transplanted hair, and attaching said non-surgical hair piece to the person's scalp.

2. The process defined in claim 1 wherein the beginning of the most forward portion of said front natural hair line are said micrografts and extending toward the back of said front natural hair line whereat the transplant grafts are minigrafts.

* * * * *